(12) United States Patent
Fung et al.

(10) Patent No.: US 6,601,748 B1
(45) Date of Patent: Aug. 5, 2003

(54) SURGICAL STAPLER

(75) Inventors: Duncan C. Fung, Richmond, VA (US); Alex C. Fung, Yuen Long (HK)

(73) Assignee: Modern Medical Equip. MFG., Ltd. (HK)

( * ) Notice: Subject to any disclaimer, the term of this patent is extended or adjusted under 35 U.S.C. 154(b) by 0 days.

(21) Appl. No.: 10/017,218

(22) Filed: Dec. 15, 2001

(51) Int. Cl.[7] ................................................. A61B 17/04
(52) U.S. Cl. ................................ 227/176.1; 227/181.1; 227/182.1; 227/19
(58) Field of Search ........................... 227/175.1, 177.1, 227/181.1, 182.1, 176.1, 19, 83, 107, 114, 120, DIG. 1

(56) References Cited

U.S. PATENT DOCUMENTS

| | | | | |
|---|---|---|---|---|
| 4,109,844 A | * | 8/1978 | Becht | 227/120 |
| 4,179,057 A | * | 12/1979 | Becht et al. | 227/19 |
| 4,411,378 A | * | 10/1983 | Warman | 227/19 |
| 4,558,810 A | * | 12/1985 | Mulhauser et al. | 227/19 |
| 4,591,086 A | * | 5/1986 | Campbell et al. | 227/19 |
| 4,669,647 A | * | 6/1987 | Storace | 227/19 |
| 4,951,860 A | * | 8/1990 | Peters et al. | 227/177.1 |

* cited by examiner

*Primary Examiner*—Scott A. Smith
*Assistant Examiner*—Nathaniel Chukwurah

(57) ABSTRACT

An improved surgical stapler including a digital counter to facilitate easy accounting of the number of staples consumed during a procedure. The surgical stapler also includes audible feedback including a first audible sound to indicate when an individual staple has been formed and a second audible sound to indicate that the stapler is ready to begin another staple forming process. The surgical stapler is of simple construction that lends itself to low cost production and mass assembly techniques thereby enabling it to be a disposable device.

14 Claims, 7 Drawing Sheets

SURGICAL STAPLER

FIELD OF THE INVENTION

This invention relates to skin and fascia staplers, and particularly to a surgical stapler that provides an improved method of counting the total number of staples that is used during a surgical procedure.

BACKGROUND OF THE INVENTION

Surgical skin or fascia staplers are well known in the medical industry. Their purpose is to join dislocated skin or fascia by inserting surgical staples along the rupture to hold the adjacent portions of skin together until the patient's natural healing processes enable the separate portions to join together. Over the years, surgeons have converted more and more to the use of surgical staples rather than conventional thread sutures for closing incisions or wounds in the skin or fascia of a patient.

Early examples of surgical staplers, such as that of U.S. Pat. No. 3,873,016 to Fishbein, issued Mar. 25, 1975, disclose a pliers-like instrument including a staple driving ram, a staple guide, and an anvil that operate from outside the severed skin. A ratchet means is provided to prevent the pliers handles from reversing or opening once a closing movement has begun. This prevents a second staple from being fed into the staple guide while the one ahead of it is still in the guide.

Early versions of surgical staplers were reusable therefore necessitating that the stapler be cleaned and disinfected when used on more than one patient. Later improvements to surgical staplers included the production of disposable models. U.S. Pat. No. 4,109,844 to Becht, issued Aug. 29, 1978 for example, discloses a surgical stapler that may be fabricated in such a way as to constitute a single-use, disposable instrument.

In the past, unfortunate incidents have occurred in the operating room where various operating devices or equipment has been left inside of the patient by mistake. In the modern-day operating room it has therefore become imperative that all operating equipment is accounted for prior to closing the operating cavity. This accounting of equipment even extends to small items such as the number of staples that have been used on a patient. U.S. Pat. No. 4,406,392 to Campbell, et al. (hereinafter the '392 patent), issued Sep. 27, 1983 addresses this accounting issue by providing an indicator to indicate the number of staples expended. Although providing a means of accounting for the staples expended, the device of the '392 patent provides only an analog readout. As can be imagined, since the stapler of the '392 patent is a disposable model it is quite compact, and the gradations on the analog scale are located in quite close proximity to one another. A user must then correctly interpolate the reading between two annotated hash marks. Considering that blood or other detritus from the operating site may occlude the viewing window above the indicator, it would be very difficult for a surgeon or assistant to determine the exact number of staples expended in a given procedure.

A further disadvantage of the prior art surgical staplers includes the fact that no audible feedback has been provided to indicate when a staple has been inserted. An audible signal would improve the utility of the device by letting surgeons know when a staple has been inserted into the ruptured skin or fascia.

SUMMARY OF THE INVENTION

The present invention comprises an improved surgical stapler including a digital counter to facilitate easy and accurate accounting of the number of staples consumed during a procedure and audible feedback to indicate when an individual staple has been inserted and when the stapler is ready to form another staple. The surgical stapler is of simple construction that lends itself to low cost production and mass assembly techniques thereby enabling it to be a disposable device.

Figure 1:
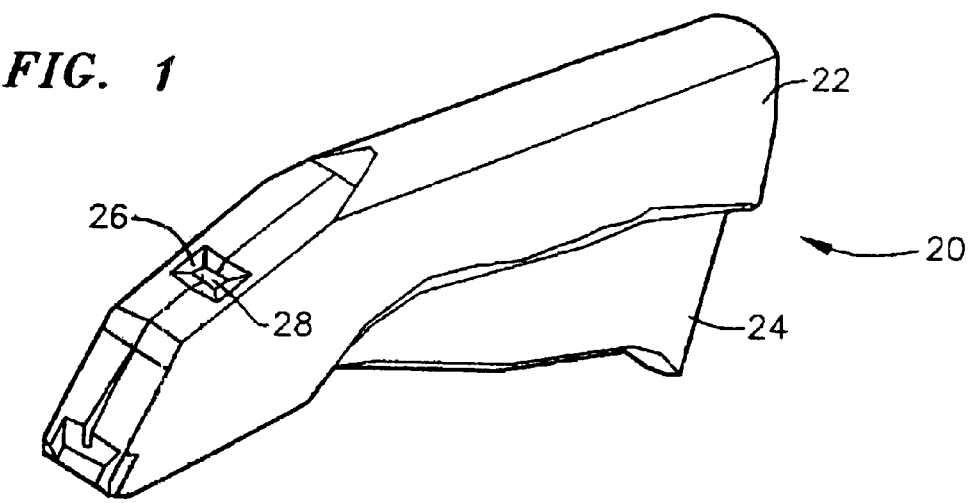
FIG. 1 and FIG. 2 are perspective views of the preferred embodiment of the surgical stapler of the present invention.

| Index to Reference Numerals in Drawings | |
|---|---|
| 20 | surgical stapler |
| 22 | housing |
| 24 | trigger |
| 24a | trigger portion |
| 26 | window |
| 28 | mechanical digital counter |
| 30 | handle |
| 32 | V-shaped spring |
| 34 | staple delivery system |
| 36 | staple forming system |
| 38 | forward portion of housing |
| 40 | staple bench |
| 42 | spring |
| 44 | spring guide pin |
| 46 | pin forwarder |
| 48 | upper forming strip |
| 50 | lower forming strip |
| 52 | first digit wheel |
| 54 | second digit wheel |
| 56 | pilot pin |
| 58 | wheel forward arm |
| 60 | stop arm |
| 62 | nub |
| 64 | depression |
| 64a | deep depression |
| 66 | first end (of wheel forward arm) |
| 68 | second end (of wheel forward arm) |
| 70 | anchored end (of stop arm) |
| 72 | free end (of stop arm) |
| 74 | outer periphery (of first digit wheel) |
| 76 | outer periphery (of second digit wheel) |

-continued

Index to Reference Numerals in Drawings

| | |
|---|---|
| 78 | first pawl (of stop arm) |
| 80 | second pawl (of stop arm) |
| 82 | long pawl (of wheel forward arm) |
| 84 | short pawl (of wheel forward arm) |
| 86 | first side (of second end of wheel forward arm) |
| 88 | second side (of second end of wheel forward arm) |
| 90 | outward facing surface |
| 92 | staple |
| 94 | digit |
| 96 | head cover |
| 98 | skin |

DETAILED DESCRIPTION OF THE INVENTION

Figure 2:
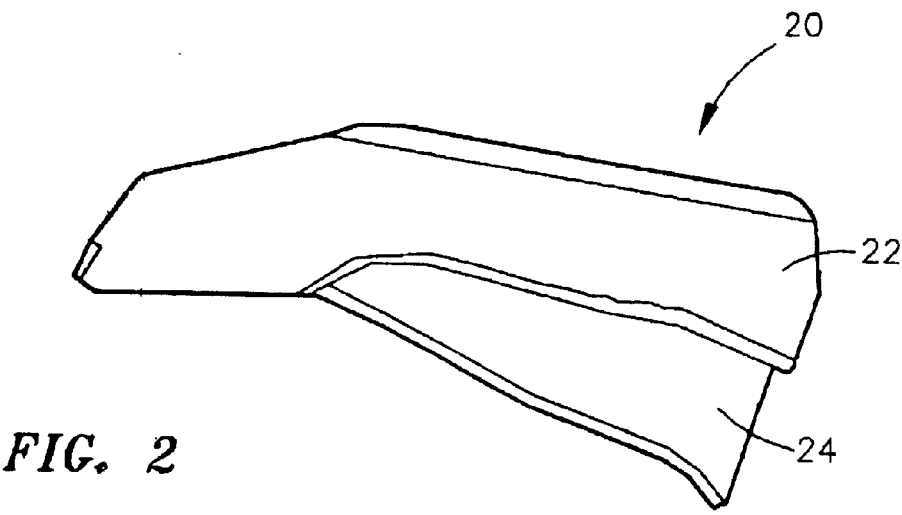

Referring to FIG. 1 and FIG. 2, the preferred embodiment of the surgical stapler 20 of the present invention includes a housing 22, a trigger 24, and a window 26 that allows viewing of a mechanical digital counter 28 that increments downward by one digit as each surgical staple is consumed. As shown in the perspective view of FIG. 1 and the top view of FIG. 3, the window 26 is well forward of the handle 30 section of the housing 22 thereby allowing unobstructed viewing of the window 26 and therefore the mechanical digital counter 28 as the stapler 20 is used.

Figure 3:
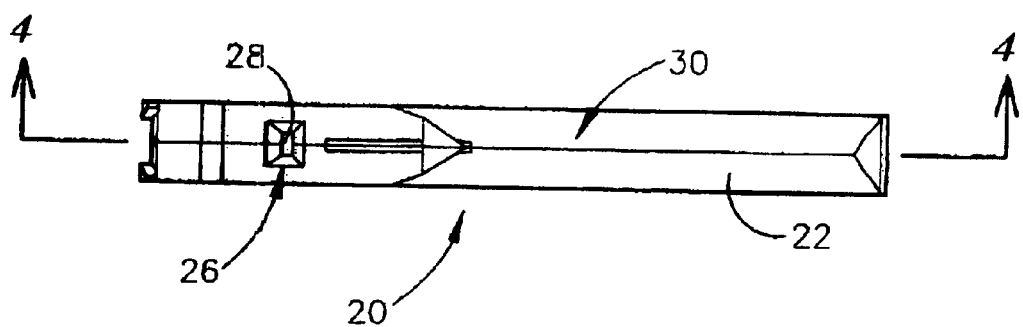
FIG. 3 is a top view of the surgical stapler of FIG. 1.
Figure 4:
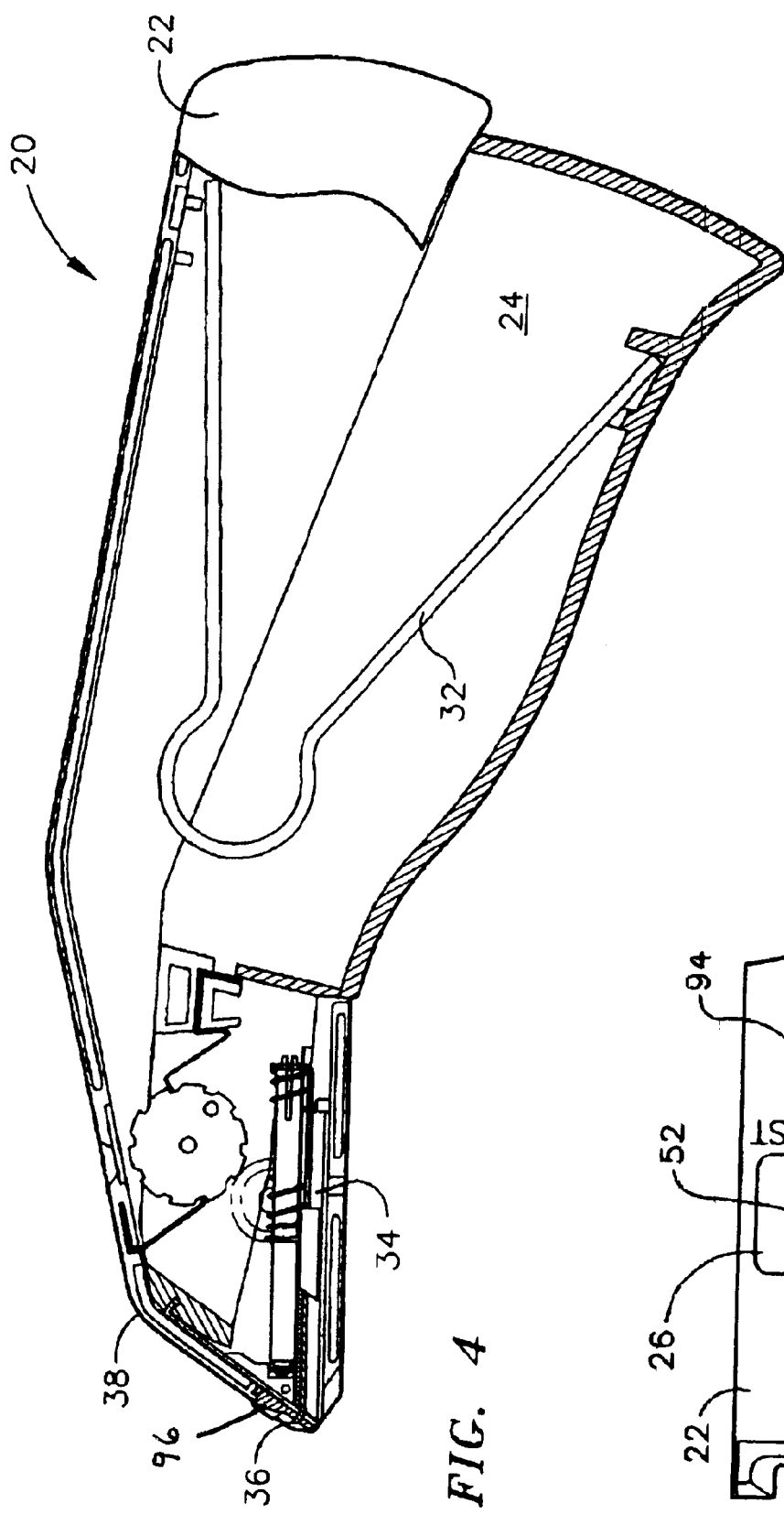
FIG. 4 is a sectional view taken along lines 4—4 of FIG.3.
Figure 5:
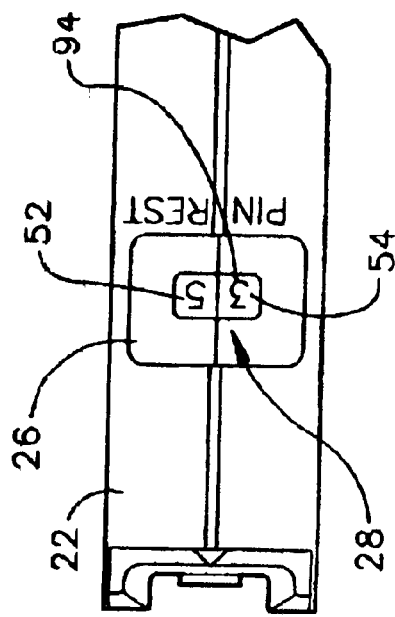
FIG. 5 is a detailed view of the digital counter portion of the surgical stapler of FIG. 1.

Referring to FIG. 4, a sectional view taken along line 4—4 in FIG. 3, the surgical stapler 20 includes a first or V-shaped spring 32 that biases the trigger 24 in an extended position away from the housing 22. A staple delivery system 34 and a staple forming system 36 are located in the forward portion 38 of the housing 22 as shown. The preferred material of construction of the V-shaped spring 32 is spring steel. A head cover 96 is provided to cover and protect the moving parts within the staple forming system 36.

Figure 6:
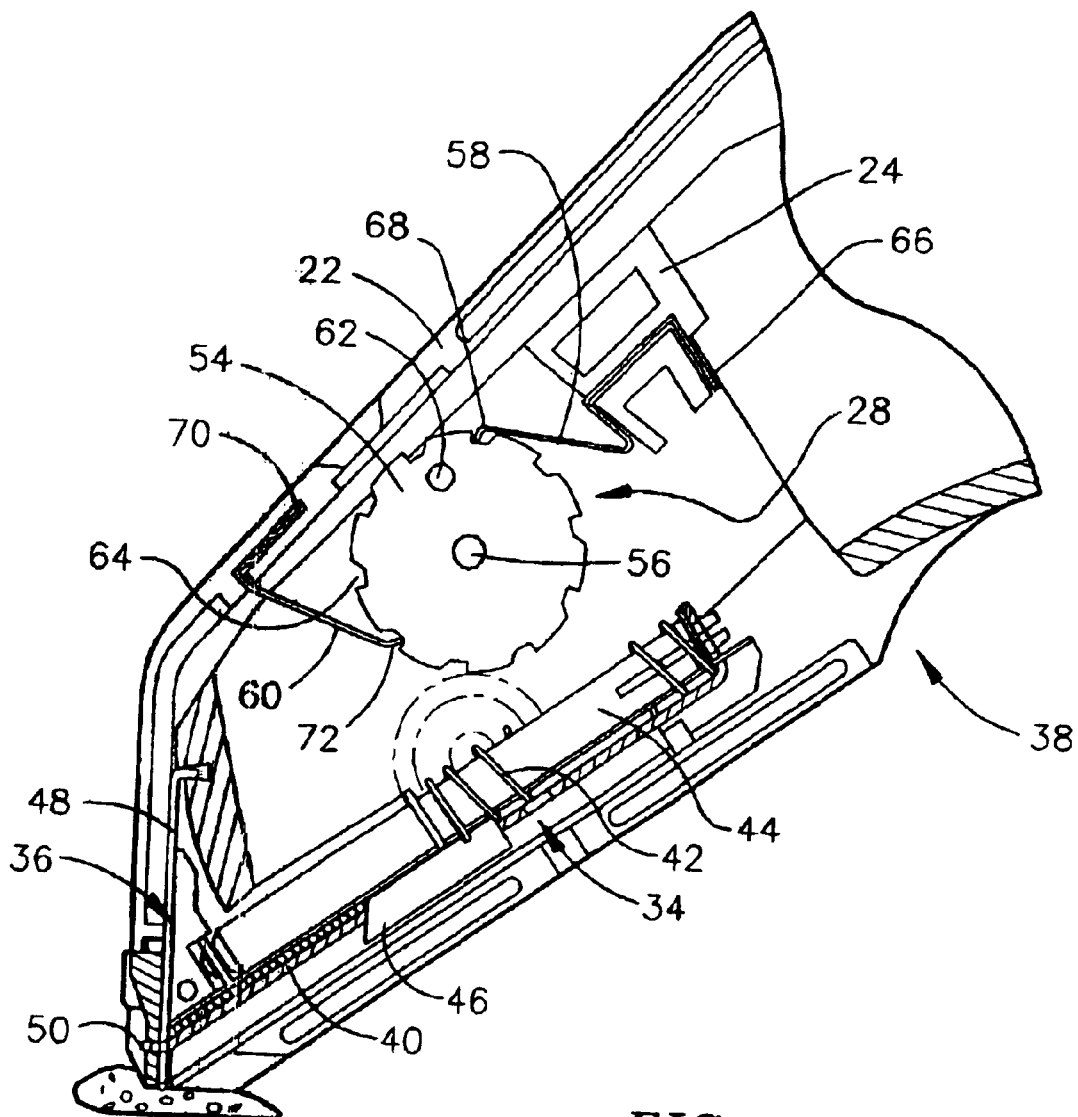
FIG. 6 is a detailed portion of the sectional view of FIG. 4 showing the details of the forward portion of the surgical stapler of FIG. 1.

Referring to FIG. 6, a detailed view of the forward portion 38 of the housing 22 depicts the staple delivery system 34 including a staple bench 40, a spring 42 mounted on a spring guide pin 44, and a pin forwarder 46. Staples are delivered from the staple delivery system 34 to the staple forming system 36 which includes an upper forming strip 48 and a lower forming strip 50. The lower forming strip 50 is typically an integral extension of the staple bench 40. A mechanical digital counter 28 consists of a first digit wheel 52 (not shown) and a second digit wheel 54 rotatably mounted adjacent to one another on a pilot pin 56 that is secured to the housing 22. The mechanical digital counter 28 also includes a wheel forward arm 58, a stop arm 60, and a nub 62 that is typically integral with and extends from the side of the second digit wheel 54 as shown. Each of the digit wheels 52, 54 include depressions in their outer peripheries such as the depressions 64 shown on the second digit wheel 54 which is visible in FIG. 6. The depressions 64 may, for example, take the form of lateral grooves in the outer peripheries of the digit wheels. The wheel forward arm 58 includes a first 66 and a second end 68 with the first end 66 secured to the trigger 24 and the second end 68 extending into one of the depressions 64 on the outer periphery of the digit wheels. The stop arm 60 includes an anchored end 70 and a free end 72 with the anchored end 70 secured to the housing 22 and the free end 72 extending into one of the depressions 64 in the digit wheels.

Figure 9:
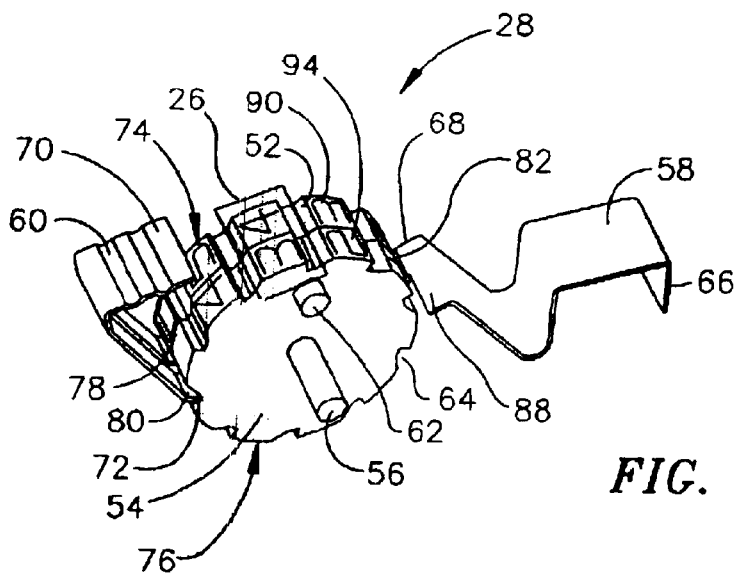
FIGS. 9, 10, and 11 are perspective views of the digital counter that shows the nub advancing to various positions as staples are formed.
Figure 10:
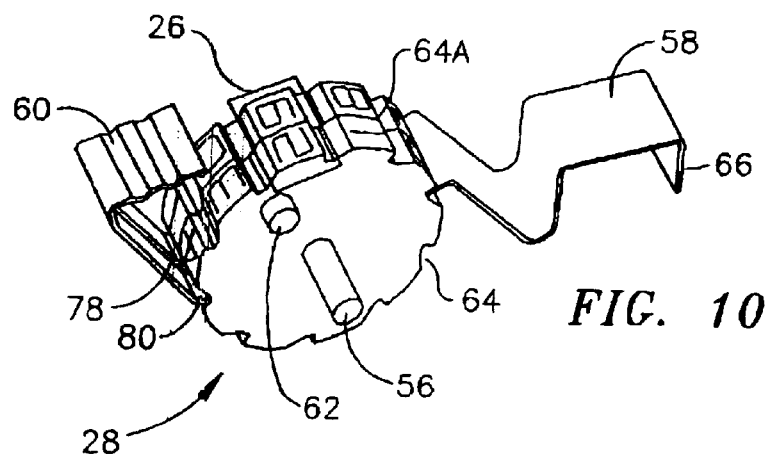
Figure 11:
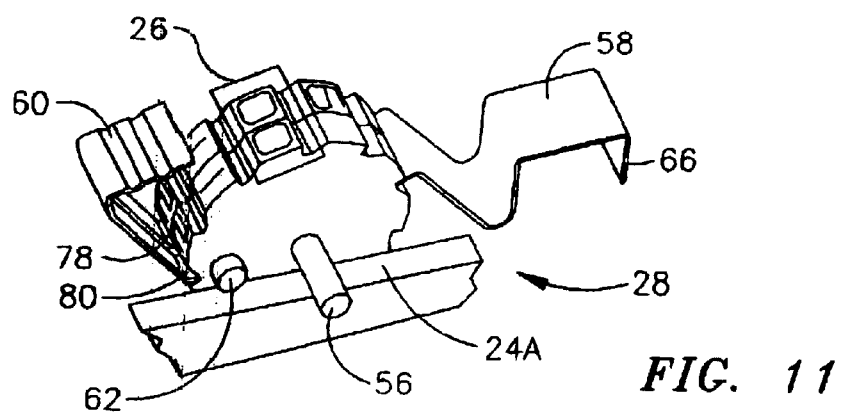

Details of the mechanical digital counter 28 can be better understood by referring to FIGS. 9 through 11. These figures show perspective views of the digital counter 28 with the first 52 and second 54 digit wheels in various states of rotation. The mechanical digital counter 28 is composed of a first digit wheel 52 and a second digit wheel 54 rotatably mounted on a pilot pin 56, a wheel forward arm 58, and a stop arm 60. Both the first 52 and second 54 digit wheels contain depressions 64 in their outer peripheries 74, 76. The second digit wheel 54 includes a nub extending from the side of the wheel away from the first digit wheel 52. Although the surgical stapler 20, including the housing 22 and trigger 24 are not shown in FIGS. 9 through 11, it should be understood that the first end 66 of the wheel forward arm 58 is secured to the trigger (not shown) and the second end 68 extends to the outer peripheries 74, 76 of the digit wheels 52, 54 and spans at least some portion of each of the wheels. The stop arm 60 includes an anchored end 70 that is secured to the housing (not shown) and a free end 72 having a first 78 and second 80 pawl that extend into one of the depressions 64 on each digit wheel 52, 54.

Figure 12:
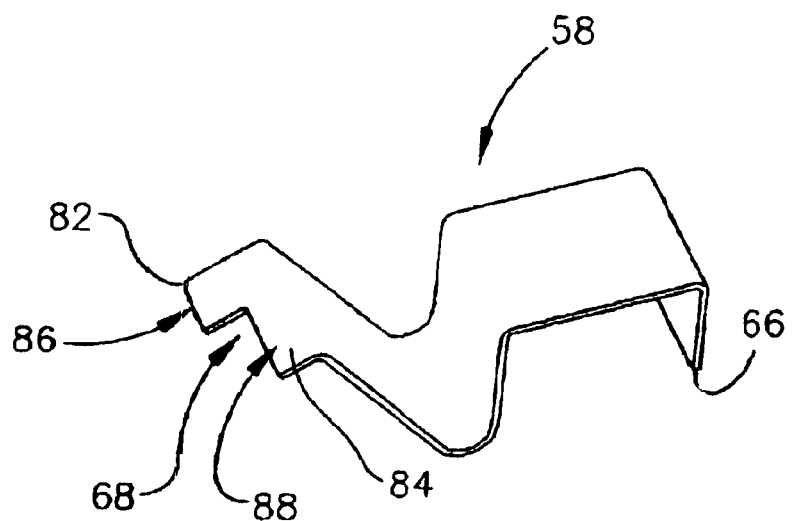
FIG. 12 is a perspective view of a wheel forward arm used in the preferred embodiment of the surgical stapler of FIG. 1.

As shown in FIG. 12, a perspective view of the wheel forward arm 58, the second end 68 of the wheel forward arm 58 includes a long pawl 82 on a first side 86 and a short pawl 84 on a second side 88.

Figure 13:
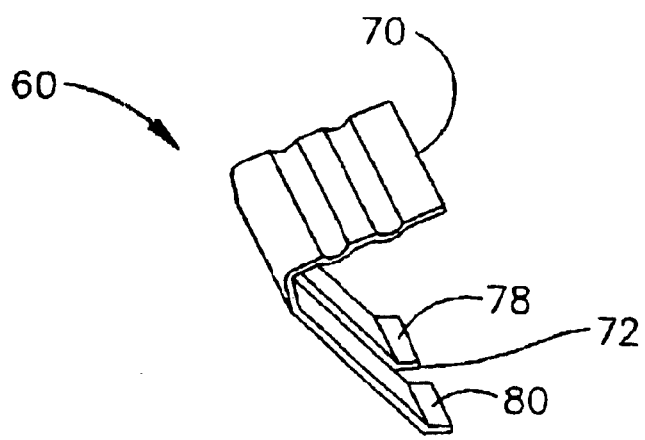
FIG. 13 is a perspective view of a stop arm used in the preferred embodiment of the surgical stapler of FIG. 1.

As shown in the perspective view of the stop arm 60 in FIG. 13, the free end 72 of the stop arm 60 includes a first pawl 78 and a second pawl 80.

Referring again to FIG. 9, the long pawl denoted by the reference numeral 82 is barely visible in this figure, but it should be understood that the long pawl 82, located on the first side 86 of the wheel forward arm 58, extends into one of the depressions 64 in the first digit wheel 52. There are typically ten depressions 64 in each digit wheel 52, 54 when the preferred embodiment of the surgical stapler is used with the Arabic numeral system. The plurality of depressions 64 in the outer peripheries of the digit wheels 52, 54 divide the outer peripheries 74, 76 into a plurality of outward facing surfaces 90. Each of the outward facing surfaces contains a digit 94 as shown. Typically, the first digit wheel 52 includes a digit 94 on each outward facing surface 90 for a total of ten digits. The second digit wheel 54 typically includes the digits zero through four, but is not restricted to these.

The principle of operation of the mechanical digital counter 28 of the present invention would best be understood by referring to FIGS. 9 through 11 in sequence. The preferred embodiment of the surgical stapler would typically be produced to hold forty surgical staples. Typically, five of the forty total staples are expended at the end of the production process for quality control purposes leaving thirty-five staples in the stapler when delivered to the user. It should be understood that the surgical stapler of the present invention may be designed to hold more or less than forty staples, but forty total staples are an adequate number to provide for both quality control purposes and for a typical medical procedure in which a surgical stapler would be used. FIG. 9 therefore depicts the mechanical digital counter 28 with the two digits for thirty-four showing through the window 26 (in ghost lines) in the housing (not shown). This is denoting that thirty-four staples remain in the surgical stapler. Upon depressing the trigger (not shown), the wheel forward arm 58 is forced forward by the movement of the trigger, and the long pawl 82, being disposed within one of the depressions 64 on the first digit wheel 52, causes the first digit wheel 52 to rotate around the pilot pin 56. The first digit wheel 52 rotates until the first pawl 78 of the stop arm 60 snaps into the next depression 64 that it encounters. A loud click is created by the stop arm 60 as it snaps into the depression 64. Since the full depression of the trigger also causes the upper forming strip (not shown) to form a staple, the action of the stop arm 60 snapping into the depression 64 coincides with the forming of a staple. The loud click created by the stop arm 60 therefore notifies the user of the surgical stapler that a staple has been formed. At this point, after the stop arm 60 has snapped into the next depression 64, the wheel forward arm 58 has reached its maximum extent of travel and the trigger is fully depressed. Release of the trigger at this point causes the wheel forward arm 58 to return to the next depression 64. As the long pawl 82 of the wheel forward arm 58 aligns with the next depression 64, the wheel forward arm 58 snaps into the depression 64 and creates a second loud click. The surgical stapler of the present invention therefore notifies the user with a first click when a staple has been formed and by a second click when the stapler is ready to begin another staple forming process. This audible confirmation or feedback enhances the visual confirmation provided by the mechanical digital counter 28. The audible clicks produced are a function of the material of construction of the stop arm 60 and wheel forward arm 58, which are typically constructed of a resilient metal strip exhibiting stiffness but also flexibility. The preferred material of construction of the stop arm 60 is stainless steel and the preferred material of construction of the wheel forward arm 58 is phosphor bronze.

A mechanism is built into the mechanical digital counter 28 to enable rotation of the second digit wheel 54 at the same time as the first digit wheel 52 has reached zero. As shown in FIG. 13, the depression 64a between the outward facing surfaces 90 containing the digits 7 and 8 on the first digit wheel 52 is much deeper than the remaining depressions 64. Therefore, when the trigger is depressed with a zero displayed on the first digit wheel 52, upon release of the trigger the second end of the wheel forward arm 58 returns to the next depression between 7 and 8. Since the depression between 7 and 8 is a deep depression 64a, the long pawl 82 falls into the deep depression 64a causing the short pawl 84 to fall into the standard depression 64 in the second digit wheel 54. With the long pawl 82 now within the deep depression 64a in the first digit wheel 52, the short pawl 84 has fallen into a standard depression 64 in the second digit wheel 54 thereby enabling the next depression of the trigger to cause the wheel forward arm 58 to advance or rotate both digit wheels 52, 54. The first digit wheel 52 may be thought of as displaying the ones digit and the second digit wheel 54 may be thought of as displaying the tens digit position in the Arabic number system. Therefore, to advance the counter from the digits thirty-four as shown in FIG. 9 to the digits twenty-nine as shown in FIG. 10, five full depressions or cycles of the trigger would be required. For the first four depressions of the trigger, the long pawl 82 would be the only pawl within the depression 64 and would therefore cause the digital counter 28 to count down successively from thirty-four to thirty. When the digits for thirty are displayed at the window 26, the long pawl 82 has fallen into the deep depression 64a between digits 7 and 8 on the first digit wheel 52. The depression between digits 7 and 8 is the deep depression 64a that causes the short pawl 84 to fall into the standard depression 64 in the second digit wheel 54. The next time the trigger is depressed both the long 82 and short 84 pawls will advance their respective digit wheels 52 and 54 and the number displayed will go from thirty to twenty-nine. After the digits for twenty-nine are displayed in the window 26, the pawls 82, 84 of the wheel forward arm 58 will return to the next depression. Since the only deep depression in the first digit wheel 52 is between the 7 and 8 digits, subsequent depressions of the trigger will advance only the first digit wheel 52 until the digital counter 28 reads twenty. With twenty displayed in the window 26, the long pawl 82 again falls into the deep depression 64a and the next time the trigger is squeezed will advance both digit wheels 52, 54 and the digits for nineteen will be displayed. The deep depression 64a in the first digit wheel 52 between digits 7 and 8 therefore provides a means to advance both digit wheels 52, 54 on the next cycle of the trigger.

As shown in FIG. 9 and FIG. 10, a nub 62 is included on the side of the second digit wheel 54 that is away from the first digit wheel 52. The nub 62 is typically integral with the second digit wheel 54 and therefore rotates with the wheel. As shown in FIG. 9, the nub 62 starts nearly even with the window 26 and every time the second digit wheel 54 is advanced by the short pawl 84, the nub 62 will be advanced in a counterclockwise manner. This can be seen by the change of the position of the nub 62 as shown in FIG. 9 and then FIG. 10. Eventually, when the digits 00 show up on the two digit wheels 52, 54, the nub 62 has made contact with a portion 24a of the trigger 24. This stops the rotation of both digit wheels 52, 54 and also stops the audible feedback from the surgical stapler as the stop arm 60 and wheel forward arm 58 will be prevented from falling into further depressions 64. The surgical stapler 20 of the present invention therefore provides both visual and audible confirmation when all staples have been consumed. The visual confirmation is through direct readout of the mechanical digital counter 28 and the audible confirmation is through a cessation of clicks on subsequent depressions of the trigger after the counter reaches 00 digits. The zero digits may also be highlighted in a color different from the color of the remaining digits, to call the user's attention to the fact that the stapler has expended all the available staples. The audible feedback provides an additional confirmation that is helpful in case blood or other operating debris obscures the window 26.

Figure 7:
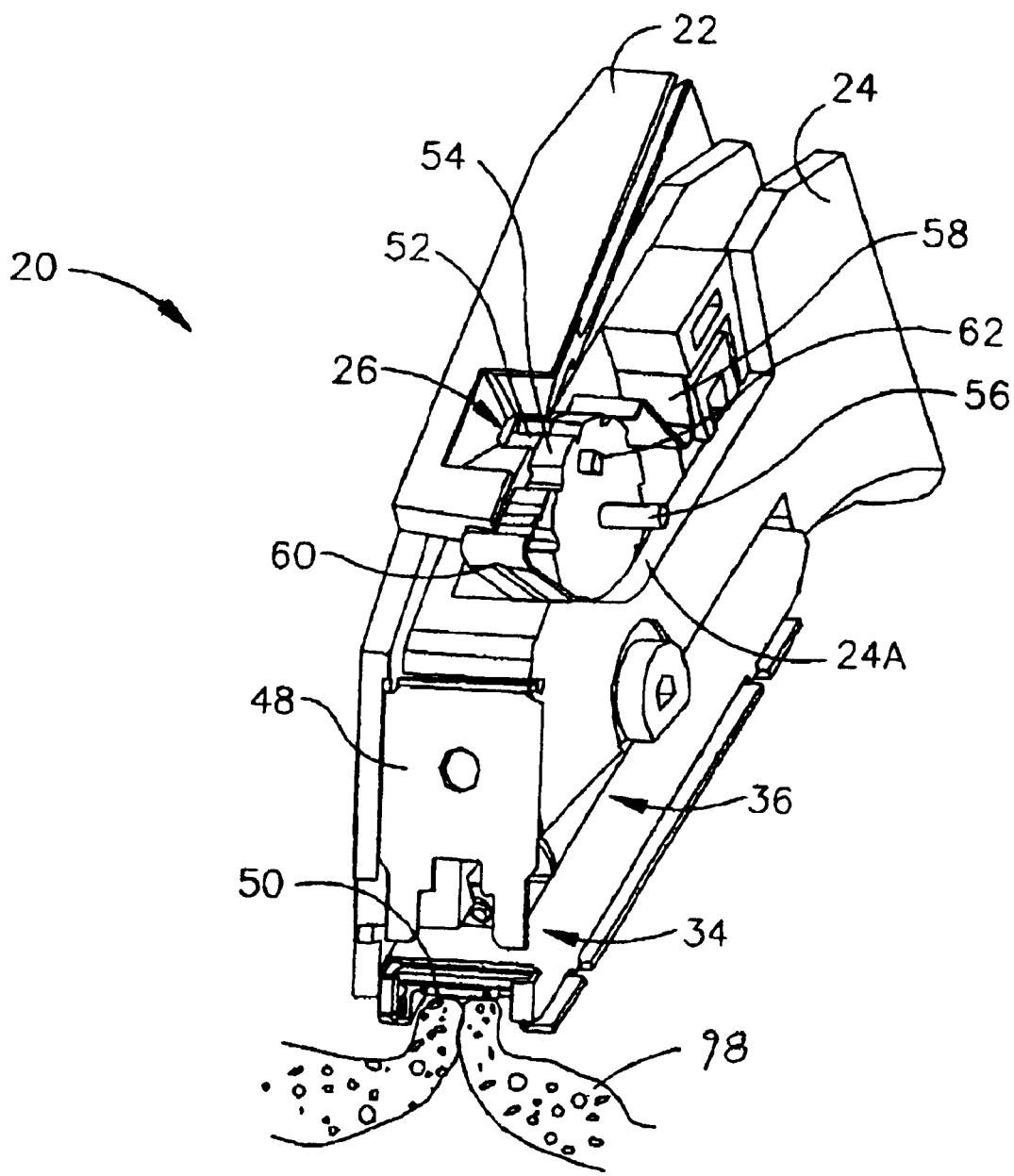
FIG. 7 is a perspective view of the surgical stapler of FIG. 1 with the trigger extended and with a portion of the forward housing cut away to show the upper forming strip in its uppermost position.

A perspective view of the surgical stapler 20 in use is shown in FIG. 7. A portion of the housing 22 has been cut away to show the trigger 24 in its extended position. At this time the upper forming strip 48, which is secured at its top end to the trigger 24, is in its uppermost position. A staple 92 is visible on top of the lower forming strip 50.

Figure 8:
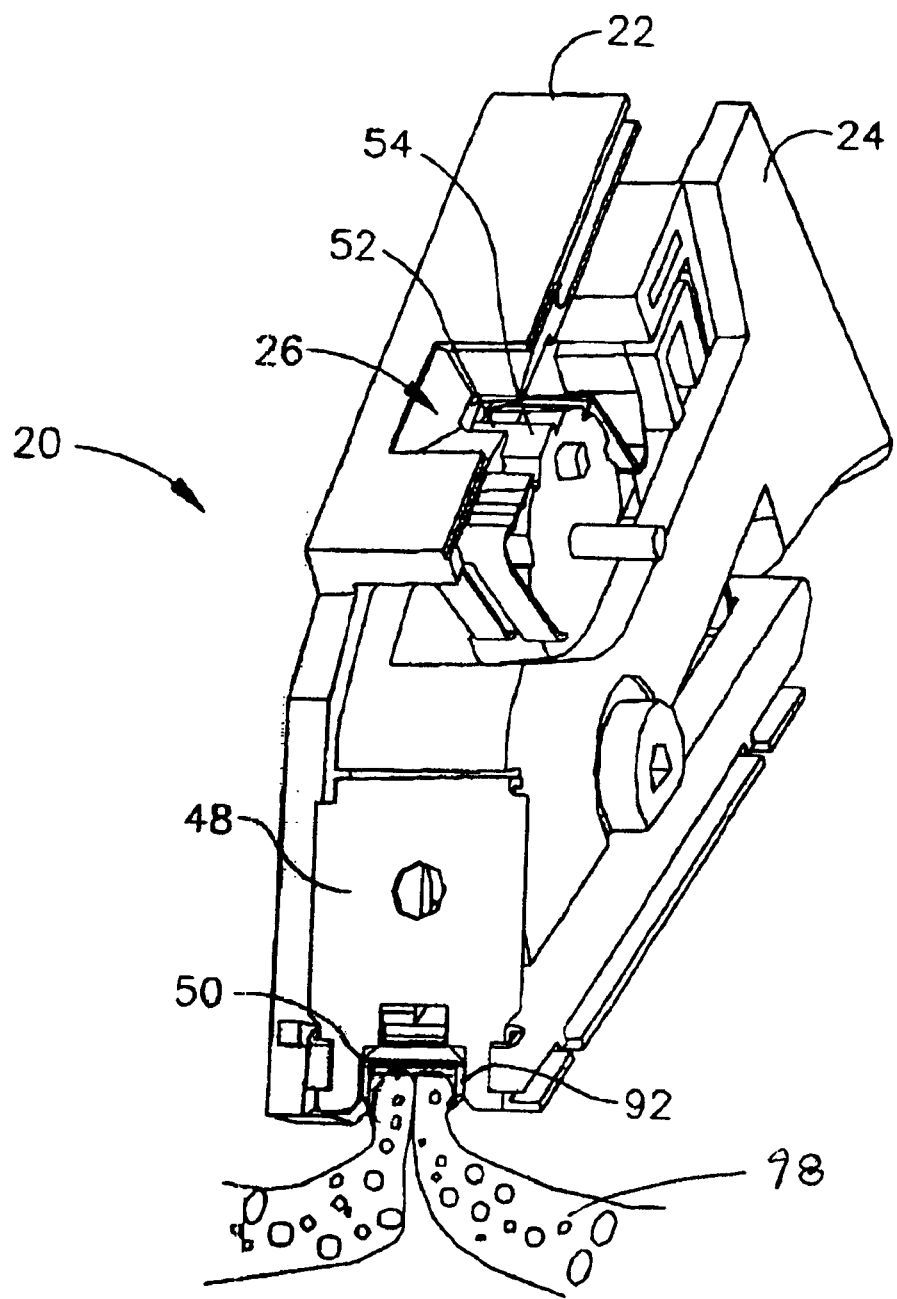
FIG. 8 is a perspective view of the surgical stapler of FIG. 1 with the trigger partially depressed and with a portion of the nose section cutaway to show the upper forming strip in a lower position forming a staple.

Referring to FIG. 8, a perspective view is shown of the surgical stapler 20 with the trigger 24 partially depressed and with a portion of the housing 22 cut away. With the trigger 24 depressed, the upper forming strip 48 has been forced down by the trigger 24 causing the staple 92 to be bent around the lower forming strip 50 therefore binding the portions of skin 98 together.

The surgical stapler 20 of the present invention therefore provides a method of inserting surgical staples into skin or fascia that includes: providing a surgical stapler including a housing, a trigger, a staple delivery system, a staple forming system and staples, providing a mechanical digital counter that increments one digit as each of the staples is consumed, providing an audible feedback system comprised of two clicks denoting the forming of a staple and the return of said trigger to its starting position to begin a new staple forming cycle, and providing a system to lock the mechanical digital counter and stop the audible clicks once all of the staples have been consumed.

Although the description above contains many specific descriptions and typical materials of construction, these should not be construed as limiting the scope of the invention but as merely providing illustrations of some of the presently preferred embodiments of this invention.

Thus the scope of the invention should be determined by the appended claims and their legal equivalents, rather than by the examples given.

What is claimed is:

1. A surgical stapler comprising:
   a housing having a pilot pin;
   a trigger pivotably connected to said pilot pin;
   a first spring which biases said trigger in an extended position away from said housing;
   a staple delivery system;
   a plurality of staples;
   a mechanical digital counter for providing a digital read-out of the number of staples remaining;
   an audible feedback system to provide an audible confirmation as each staple is consumed;
   a first digit wheel rotatably mounted on said pilot pin;
   a second digit wheel rotatably mounted on said pilot pin adjacent to said first digit wheel;
   a plurality of depressions in the outer peripheries of said wheels dividing said outer peripheries into a plurality of outward facing surfaces;
   a digit located on each of said outward facing surfaces;
   a wheel forward arm having a first and a second end;
   a stop arm having an anchored and a free end, said anchored end secured to said housing, said free end including a pawl extending into one of said depressions;
   a window in said housing enabling the viewing of two of said digits side by side consisting of one digit from said second digit wheel and one digit from said first digit wheel;
   a long pawl on a first side of said forward arm facing said first digit wheel; and
   a short pawl on a second side of said forward arm facing said second digit wheel; wherein said first end of said wheel forward arm is secured to said trigger and said second end of said wheel forward arm extends to the outer periphery of said wheels and spans at least some portion of each of said wheels.

2. The surgical stapler of claim 1 wherein said long pawl extends into a first of said depressions in said first digit wheel when said trigger is fully extended.

3. The surgical stapler of claim 2 wherein depression of said trigger causes said long pawl to engage said first depression in said first digit wheel thereby rotating said first digit wheel until said pawl of said stop arm engages an adjacent depression on said first digit wheel thereby stopping rotation of said first digit wheel.

4. The surgical stapler of claim 3 wherein release of said trigger enables said long pawl of said wheel forward arm to escape said first depression and return to and engage a second depression to enable the next cycle of said trigger.

5. The surgical stapler of claim 1 wherein said audible feedback system is comprised of:
   a first clicking sound created by said pawl of said stop arm snapping into one of said depressions; and
   a second clicking sound created by said long pawl of said wheel forward arm snapping into one of said depressions in said first digit wheel.

6. The surgical stapler of claim 5 wherein said first clicking sound is created at essentially full depression of said trigger and said second clicking sound is created just prior to full release of said trigger.

7. The surgical stapler of claim 6 wherein said first clicking sound indicates that one of said staples has been formed and said second clicking sound indicates that said stapler is ready to begin another staple forming process.

8. The surgical stapler of claim 5 wherein said clicking sound is enhanced by the preferred materials of construction of said stop arm and said wheel forward arm.

9. The surgical stapler of claim 8 wherein said preferred material of construction for said stop arm is stainless steel.

10. The surgical stapler of claim 8 wherein said preferred material of construction for said wheel forward arm is phosphor bronze.

11. The surgical stapler of claim 1 wherein said plurality of depressions in said first digit wheel includes a plurality of shallow depressions and one deep depression such that when said long pawl engages said deep depression of said first digit wheel, said short pawl engages a depression in said second digit wheel thereby causing said wheel forward arm to rotate both said digit wheels and thereby advance said digits on said outward facing surfaces of said digit wheels.

12. The surgical stapler of claim 11 wherein said first digit wheel corresponds to the ones digit and said second digit wheel corresponds to the tens digit when said mechanical digital counter is used with the Arabic numeral system.

13. The surgical stapler of claim 1 wherein said second digit wheel contains a nub extending from its side, said nub stops rotation of said first digit and second digit wheels after all of said staples have been consumed and thereby also ends audible feedback from said arms.

14. A surgical stapler comprising:
   a housing having a pilot pin;
   a trigger pivotably connected to said pilot pin;
   a first spring which biases said trigger in an extended position away from said housing;
   a staple delivery system;
   a plurality of staples;
   a mechanical digital counter for providing a digital read-out of the number of staples remaining;
   an audible feedback system to provide an audible confirmation as each staple is consumed;
   a first digit wheel rotatably mounted on said pilot pin;
   a second digit wheel rotatably mounted on said pilot pin adjacent to said first digit wheel;
   a plurality of depressions in the outer peripheries of said wheels dividing said outer peripheries into a plurality of outward facing surfaces;
   a digit located on each of said outward facing surfaces;
   a window in said housing enabling the viewing of said digits on said wheels;
   a wheel forward arm having a first and a second end;
   a long pawl on a first side of said forward arm facing said first digit wheel; and
   a short pawl on a second side of said forward arm facing said second digit wheel; wherein said first end of said wheel forward arm is secured to said trigger and said second end of said wheel forward arm extends to the outer periphery of said wheels and spans at least some portion of each of said wheels.

* * * * *